Figure 1:
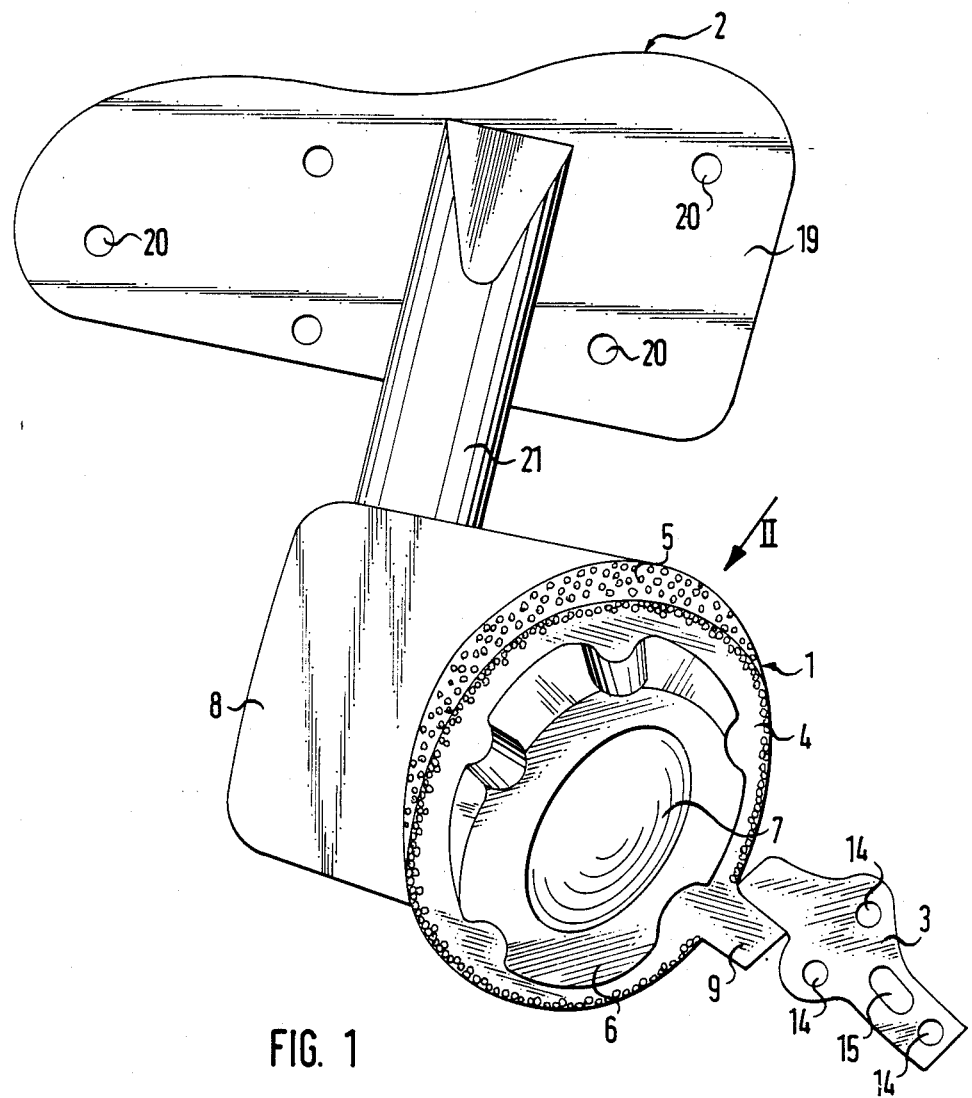

United States Patent [19]
Grundei et al.

[11] Patent Number: 4,883,489
[45] Date of Patent: Nov. 28, 1989

[54] PELVIS PART PROSTHESIS

[75] Inventors: Hans Grundei, Lübeck; Erwin Hipp; Bernd Heinhuber, both of Munich, all of Fed. Rep. of Germany

[73] Assignee: S&G Implants GmbH, Lübeck, Fed. Rep. of Germany

[21] Appl. No.: 192,518
[22] PCT Filed: Aug. 29, 1987
[86] PCT No.: PCT/DE87/00387
  § 371 Date: Apr. 29, 1988
  § 102(e) Date: Apr. 29, 1988
[87] PCT Pub. No.: WO88/01491
  PCT Pub. Date: Mar. 10, 1988

[30] Foreign Application Priority Data
  Sep. 2, 1986 [DE] Fed. Rep. of Germany ....... 3629799

[51] Int. Cl.⁴ .............................................. A61F 2/34
[52] U.S. Cl. ................................................ 623/22
[58] Field of Search ................... 623/16, 18, 19, 22, 623/23

[56] References Cited
U.S. PATENT DOCUMENTS
4,743,262  5/1988  Tronzo ................................. 623/22

FOREIGN PATENT DOCUMENTS
2809556  2/1980  Fed. Rep. of Germany ........ 623/18
3027063  2/1982  Fed. Rep. of Germany ........ 623/18
3205526  9/1983  Fed. Rep. of Germany ........ 623/18
2225141 11/1974  France ................................. 623/18
1123682 11/1984  U.S.S.R. .............................. 623/22
2016275  9/1979  United Kingdom ................. 623/18

Primary Examiner—Richard J. Apley
Assistant Examiner—David J. Isabella
Attorney, Agent, or Firm—Balogh, Osann, Kramer, Dvorak, Genova & Traub

[57] ABSTRACT

A pelvis part prosthesis comprises an essentially hemispherically-shaped shell portion provided with two formed appendices, each of which has a positioning aperture and two connection elements connected to the appendices, and each being provided with a pin inserted with a self-locking tight fit in the positioning apertures. The connection elements are preferably designed as curved plates. The material layer, adjacent to the residual bone material of the pelvis, of the aforementioned parts of the prosthesis, may be in the shape of an open-cell structure to allow the bone material to grow into said structure.

3 Claims, 4 Drawing Sheets

PELVIS PART PROSTHESIS

The invention relates to a pelvis part prosthesis for replacement of a pelvis section in the area of the hip joint, comprising a shell portion for reception of a hip joint ball and connection elements joined thereto for securing the prosthesis in the area of pubic ilium.

A pelvic section prosthesis which is constructed in accordance with a modular principle, is disclosed in the German specification as laid open DE No. - 28 09 556 B2. It comprises a substantially block-shaped principal member having a reception space for the hip joint socket and several connection surfaces provided with holes and several pin-shaped connection elements, which are fastened in the holes on the one hand, and are connected on the other hand to the remanent pelvic bone material of the patient.

The principal member of the prosthesis is a comparatively large block member since it has to have several holes for the pin-shaped connection elements so that these elements may be secured in a selected hole depending on the conditions encountered with the patient. Furthermore, the connection elements inserted into the holes are fastened to the principal member by means of screws, for which purpose supplemental tapped holes have to be provided in the principal member. Although a whole prosthesis adapted in its configuration to the prevailing requirements in accordance with the conditions encountered with the patient may be put together with these prosthesis elements, this procedure is onerous and time-consuming, because the connection elements are not as readily accessible with the principal member in the implanted condition. If the prosthesis elements selected are assembled before the implanting operation, an optimum position of the elements of the prosthesis with respect to each other and thus an optimum functionality of the whole prosthesis in the body of the patient cannot always be assured. The reason is because the principal member is anchored on the pelvic bone material by means of at least three connection elements. With such connections, it is uncertain whether each connection element can be anchored reliably in the pelvic bone material because of its unfavourable structure after bone resection. Furthermore, the tapped holes and the fastening screws represent a supplemental production cost in the manufacture of the prosthesis.

The object of the invention consists in the improvement of an endoprosthesis of the kind defined in the foregoing which assures that the prosthesis may be implanted rapidly and in simple manner as well as with the result of an optimum functionality in the implanted state.

The resolution of the problem derives from the endoprosthesis which and is characterized in that the shell portion has two integrally formed appendices comprising a reception bore in each case, and that the connection elements joined to the appendices each have a pin and are installed with this pin in the reception bores in a self-locking tight fit.

In a preferred embodiment of the endoprosthesis according to the invention, each tight fitting joint between the hemispherically formed shell portion and the connection elements consists of a taper joint. The metal connection elements have spatially curved plate elements comprising holes for connection by means of screws on the corresponding bone regions. The boneside material layer of the shell portion as well as of the connection elements may complementally be formed as an open-celled structure for the growing-in of bone material.

The endoprosthesis according to the invention, whereof the parts are available in different sizes for utilization of an anatomically individually adapted prosthesis, may be implanted rapidly with an uncomplicated manner, because the final immobilization of the connection elements, may be performed by means of a self-locking tight fit without protracted assembling operations and may in each case be carried out by means of a sharp blow. The prosthesis elements may furthermore be implanted more easily in optimum manner as regards position based on no more than two connection elements to allow easier alignment of the shell portion. Furthermore, the proposed prosthesis may be produced more economically, since supplemental tapped holes with fastening screws appertaining thereto for securing the connection elements are omitted in the shell portion.

Figure 2:
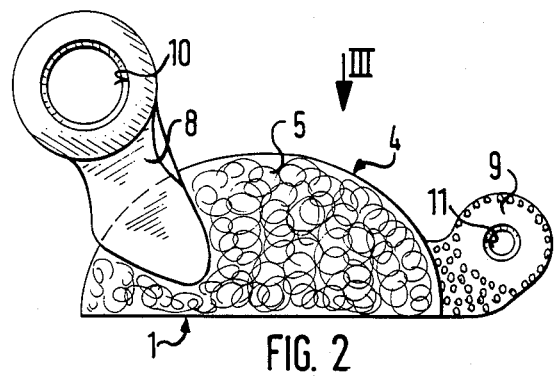
Figure 5:
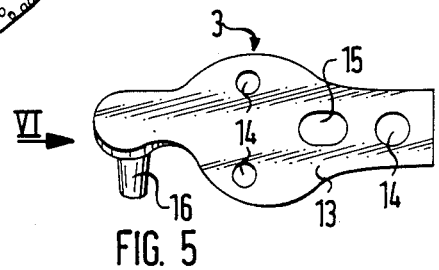
Figure 3:
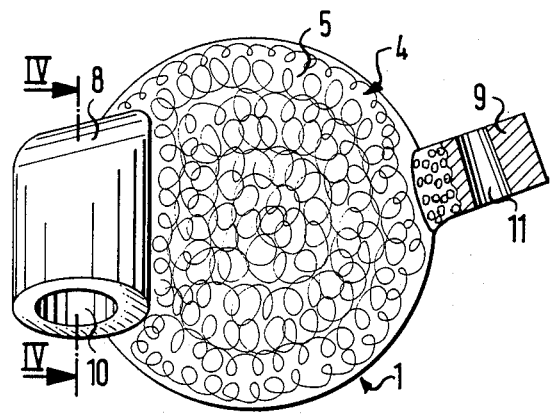
Figure 6:
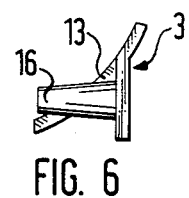
Figure 4:
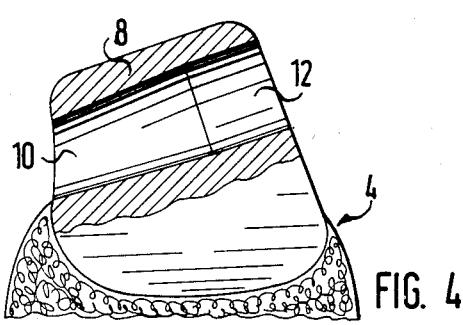
Figure 7:
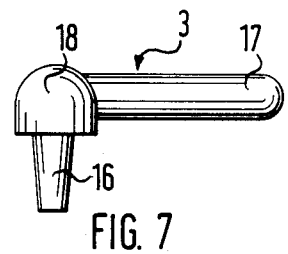
Figure 8:
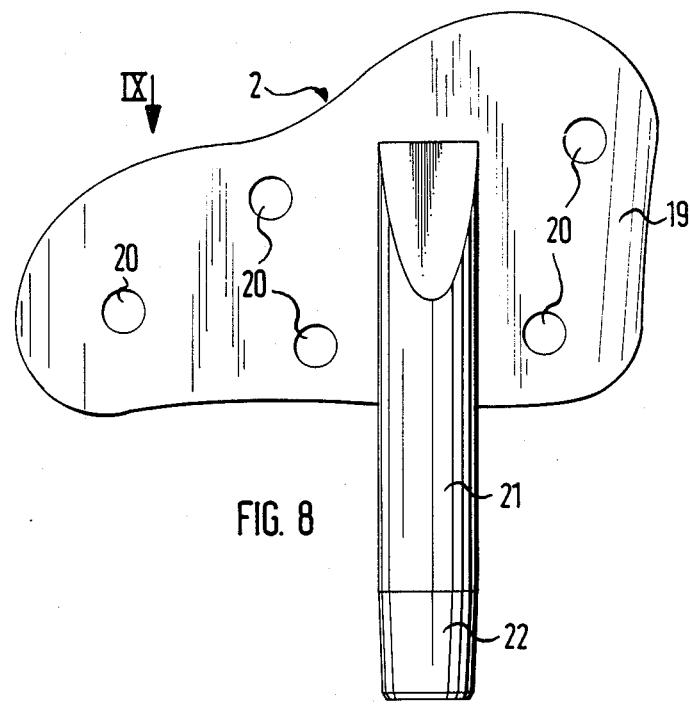
Figure 9:
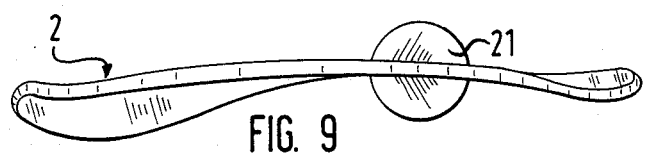
Figure 10:
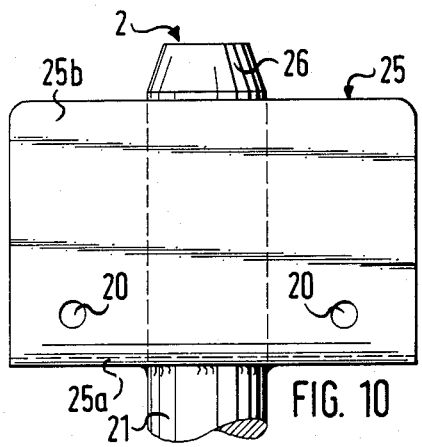
Figure 11:
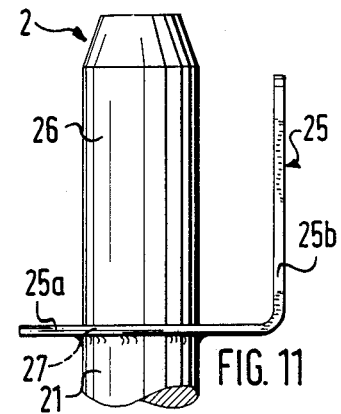
Figure 12:
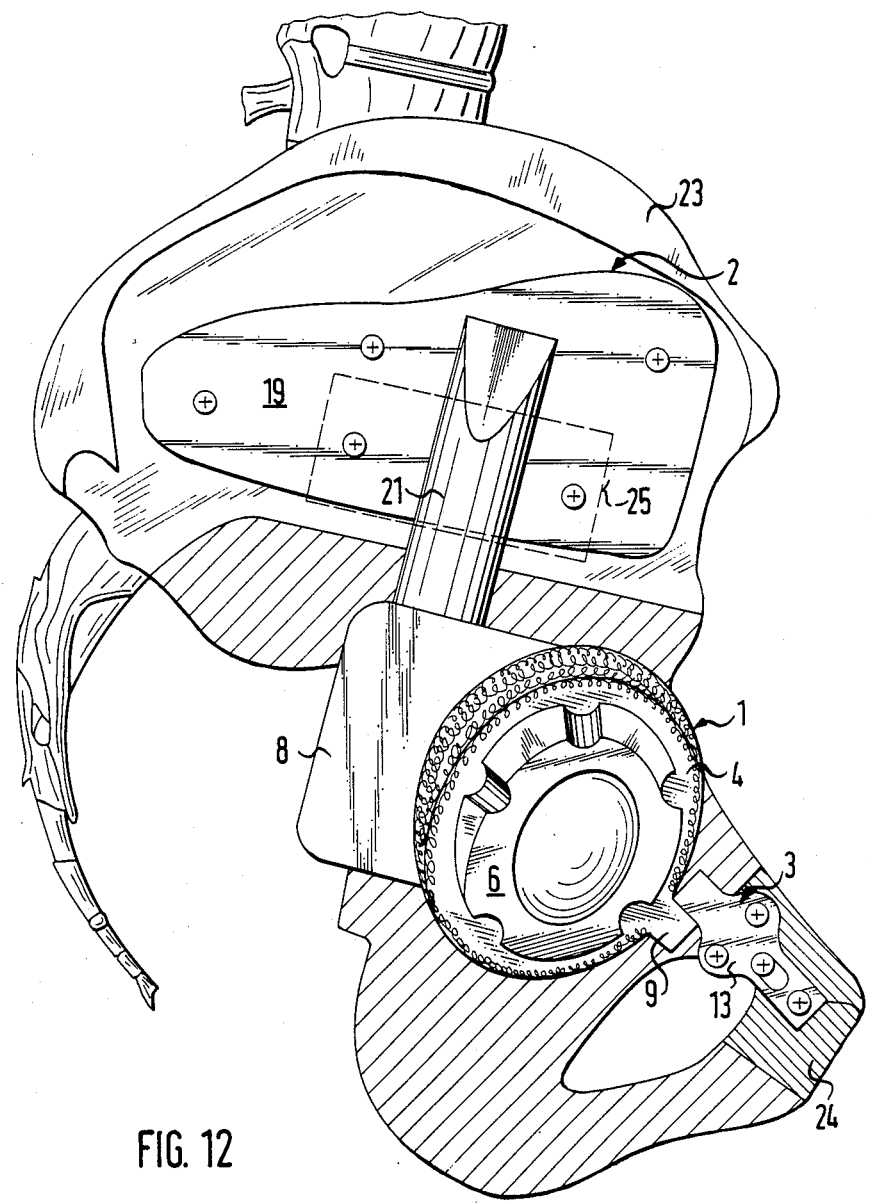

The invention is described in particular with reference to an example of embodiment illustrated in the accompanying drawings. In these:

FIG. 1 shows the example of embodiment in sideview,

FIG. 2 shows a view of a first prosthesis element according to the arrow II in FIG. 1, FIG. 3 shows a view according to the arrow III in FIG. 2, FIG. 4 shows a partial cross-sectional view along the line IV—IV in FIG. 3, FIG. 5 shows a sideview of a second prosthesis element of the example of embodiment, FIG. 6 shows a view according to the arrow VI in FIG. 5, FIG. 7 shows another form of embodiment of the second prosthesis element in sideview, FIG. 8 shows a sideview of a third prosthesis element of the example of embodiment, FIG. 9 shows a view according to the arrow IX in FIG. 8, FIGS. 10 and 11 show an alternative to the third detail in front and side view respectively, FIG. 12 shows the example of embodiment according to FIG. 1 in the implanted state.

According to FIG. 1, the endoprosthesis for replacement of a human pelvic section in the region of the hip joint consists of several interconnectible principal components produced in a modular mode of construction, that is to say, comprising a shell portion 1 for reception of an artificial hip joint ball which is not shown, a connection element 2 for fastening to the ilium and another connection element 3 for connection to the os pubis.

The shell portion module 1 substantially comprises a hollow hemisphere of metal 4, for example high-grade alloyed steel with utilization of chromium, cobalt and molybdenum, in which at least the layer of material forming the external surface of the hemisphere may be formed as an open-celled structure 5 for the growing-in of bone material. An equally hemispherical socket 6 of plastics material, e.g. of polyethylene, whereof the cavity 7 receives an artificial hip joint ball (not shown) is anchored in the shell volume of the hemisphere.

The shell portion 1 has an appendix 8 and 9 formed integrally at each of two approximately mutually opposed points of its circumference, which appendices are constructed for connection to the connection elements 2 and 3, respectively. FIGS. 2,3 and 4 show enlarge details in this respect. It is apparent therefrom that the appendices 8,9 are formed by an one-piece casting, jointly with the hemisphere 4, the appendices being formed in the manner of a pedestal bearing and each having a reception bore 10 and 11 for reception of the corresponding connection element. The reception bores 10,11 are produced as tapered bores which cooperate with tapered pins of the connection elements, as will be described. The tapered reception bore 10 of the ilium-side appendix 8 need not be made tapering throughout its length, but may also have a cylindrical portion 12. As for the rest, the appendix 8 need not necessarily be provided with an open-celled structure in the area of its surface.

FIGS. 5, 6 and 7 show forms of embodiment for the connection elements 3 at the side of the os pubis. The form of embodiment according to FIGS. 5 and 6 comprises an elongated, spatially curved plate section 13 having several holes 14,15 for connection by means of screws to the os pubis (FIG. 10). The hole 15 is formed as a slot to allow of setting up a precise position of the connection element 3 on the os pubis before it is finally screwed tight. A taper pin which is driven into the reception bore 11 of the appendix 9 of the shell portion 1, is provided at one extremity of the plate section 13.

The connection element 3 described in the foregoing as well as the connection element 2 according to FIG. 7, are formed from the same material as the shell portion. Furthermore, the boneside material layer of these elements may supplementally be formed as an open-celled structure for the growing-in of bone material. These elements, except for their pins 16, may alternately also be produced as elements having an open-celled structure throughout.

The alternate connection element 3 according to FIG. 7 has a finger-like projection 17 of circular cross-section, with a mainly hemispherical head 18 at its one extremity, which bead carries the already referred to pin 16 extending at right angle to said projection. Whereas the finger-like projection 17 is implanted into a corresponding recess of the prepared os pubis, the tapered pin 16 engages in the tapered reception bore 11 of the appendix 9.

The connection element, according to FIGS. 8 and 8, produced from the same material as the other elements 1 and 3. The connection element comprises an approximately triangular plate section 19 curved a little spatially, comprising several holes 20 and a shank 21 which has a taper 22 on its free terminal portion. Whereas the plate section 19 is fastened on the appropriately prepared ilium, the shank 21 engages with its taper 22 in the tapered reception bore 10 of the appendix 8 in a powerful friction lock (FIG. 1). The shank 21 extends over the plate section 19 at its rear side only, as shown in FIG. 8, so that the side of the plate section 19 which is subsequently in contact with the ilium, is not covered by the shank material. This plate section 19 may also consist of an opencelled structure, at least in its marginal layer subsequently facing towards the ilium; it may however also be made in the form of an open-celled structure throughout.

Although it is preferable to join the connection elements 2 and 3 to the shell portion module by means of the tight taper fit shown and described, it is also possible to utilize a gripping joint of the kind in which the gripping force is generated by means of screws, the appendices 8 and 9 then being slotted correspondingly for this purpose.

An alternative to the connection element 2 is shown in figures 10 and 11. The plate section is formed as an L-shaped plate element 25, two branches 25a and 25b thus produced extending approximately at right angle to each other. The branches as such may be plane as shown, or may also be spatially curved. The shank 21 already referred to earlier in the foregoing and comprising a gripping stud which is provided at the one side of the one branch 25a, whereas at least one projecting anchoring element 26 is provided at the other side of this branch. Several mutually spaced-apart anchoring elements 26 may also be provided. As shown in FIGS. 10 and 11, the anchoring elements 26 which is implanted in an appropriately prepared recess of the ilium, and the vertical branch 25b of the plate section 25, extend approximately parallel to each other. These parts may however also have a different inclination with respect to each other, if the conditions imposed by anatomical or disease factors require this. When this alternate connection element 2 is implanted, the ilium bears on the horizontal branch 25a of the plate section 25 whereas the vertical branch 25b bears on the ilium laterally, as shown in broken lines in FIG. 12.

An uncomplicated form of embodiment of the anchoring element 26 consists in that the shank 21 is produced with an upward extension. The branch 25a then has a perforation 27 through which the shank 21 extends, the shank portion above the branch 25a forming the anchoring element. In this case, the shank is welded to the branch 25a.

Alternately, the plate section 25, the shank 21 and the anchoring element 26 may also be formed as an one-piece casting.

In the case shown, the anchoring element 26 is cylindrically formed. However, it may have other cross-sectional shapes and other external shapes. Further the bone-side marginal layer of the anchoring element may be produced as an open-celled structure for the growing-in of bone material, which may also be so in the case of the L-shaped plate section 25. Alternately, and apart from the shank 21, this anchoring element may also be produced throughout as an open-celled-structure member. Finally, the plate section 25 is also provided with several holes 20 for its attachment to the ilium.

FIG. 12 shows an implanted endoprosthesis of the kind described in the foregoing. After the diseased bone sections in the hip joint region of the pelvic bone structure have been removed according to the hatched portion and the contact surfaces for the connection elements 2 and 3, i.e. for their plate sections 19 and 13 respectively have been prepared on the ilium 23 and the os pubis 24 respectively, the endoprosthesis whereof the separate parts 1,2 and 3 may also be joined together thanks to previously performed determination of their individual size, shape and reciprocal position, being screwed to the corresponding pelvic bones 23,24.

It is apparent that the individual prosthesis elements may vary in their shape and size to allow of utilization of the most suitable prosthesis elements and thus of the corresponding endoprosthesis in accordance with the anatomical conditions of the hip joint region in question.

We claim:

1. Pelvis part prosthesis for replacement of a pelvis section in the area of the hip joint of a human being, comprising a shell portion for the reception of an artificial hip joint ball and two connection elements mechanically joined to the shell portion for securing the prosthesis in the areas of the os pubis and the ilium, respectively, characterized in that the shell portion is formed as a hollow metal hemisphere having two outer integrally formed appendices spaced about said hemisphere at positions near the os pubis and the ilium, each having a conically formed reception bore, and that said two connection elements comprise metal plates which are formed such to adapt securing faces to remaining bone material of the os pubis and ilium, respectively, and which are provided with holes for receiving screws on said securing faces, and pin means having conically formed ends to be secured in respective conically formed reception bores of said appendices by means of a self-locking tight fit.

2. Pelvis part prosthesis according to claim 1, characterized in that said connection elements consist of spatially curved metal plates.

3. Pelvis part prosthesis according to claim 1, characterized in that the connection element to be secured to the os ilium is formed by an L-shaped metal plate, one branch of which is secured at the pin of said connection element such that a portion of said pin projects through said one branch and serves as an anchoring element, and the other branch of which extends substantially parallel to said pin.

* * * * *